United States Patent
Farnam, III et al.

(10) Patent No.: US 7,674,616 B2
(45) Date of Patent: Mar. 9, 2010

(54) DEVICE AND METHOD FOR MEASURING PROPERTIES OF A SAMPLE

(75) Inventors: W. Edward Farnam, III, Flagstaff, AZ (US); Maria C. Navarro, Redwood City, CA (US)

(73) Assignee: Hemosense, Inc., San Diego, CA (US)

( * ) Notice: Subject to any disclaimer, the term of this patent is extended or adjusted under 35 U.S.C. 154(b) by 335 days.

(21) Appl. No.: 11/532,072

(22) Filed: Sep. 14, 2006

(65) Prior Publication Data
US 2008/0124749 A1    May 29, 2008

(51) Int. Cl.
*G01N 33/533*    (2006.01)
(52) U.S. Cl. .............. 435/287.1; 435/7.1; 435/7.21; 435/91.1; 435/91.2; 435/810; 435/287.2; 435/287.7; 435/287.8; 436/514; 436/518; 436/517; 436/538; 436/807; 422/68.1; 422/50; 422/55; 422/58
(58) Field of Classification Search .............. 435/7.1, 435/7.21, 91.1, 91.2, 810; 422/68.1, 50, 422/55, 58; 436/527, 538, 807
See application file for complete search history.

(56) References Cited

U.S. PATENT DOCUMENTS

| | | | |
|---|---|---|---|
| 3,674,012 A | 7/1972 | Sage | |
| 3,699,437 A | 10/1972 | Ur | |
| 3,911,728 A | 10/1975 | Fixot | |
| RE30,007 E | 5/1979 | Steuer et al. | |
| 4,301,412 A | 11/1981 | Hill et al. | |
| 5,418,141 A | 5/1995 | Zweig et al. | |
| 5,447,440 A | 9/1995 | Davis et al. | |
| 5,494,639 A | 2/1996 | Grzegorzewski | |
| 5,580,794 A | 12/1996 | Allen | |
| 5,601,995 A | 2/1997 | Exner | |
| 5,628,961 A | 5/1997 | Davis et al. | |
| 5,629,209 A | 5/1997 | Braun, Sr. et al. | |
| 5,726,026 A * | 3/1998 | Wilding et al. | 435/7.21 |
| 5,876,675 A * | 3/1999 | Kennedy | 422/99 |
| 6,046,051 A | 4/2000 | Jina | |
| 6,060,323 A | 5/2000 | Jina | |
| 6,066,504 A | 5/2000 | Jina | |
| 6,274,337 B1 * | 8/2001 | Parce et al. | 435/29 |
| 6,338,821 B1 | 1/2002 | Jina | |
| 6,613,286 B2 * | 9/2003 | Braun, Sr. et al. | 422/102 |
| 6,673,622 B1 | 1/2004 | Jina | |

(Continued)

FOREIGN PATENT DOCUMENTS

EP    1151268 B1    12/2004

(Continued)

OTHER PUBLICATIONS

Evaluation Report. SmartCheck INR Systems. NHS Purchasing and Supply Agency. Jul. 2007; 1-32.

*Primary Examiner*—Bao-Thuy L Nguyen
(74) *Attorney, Agent, or Firm*—Wilson Sonsini Goodrich & Rosati

(57) ABSTRACT

Test strips designed to prevent or reduce false results when measuring the condition of a sample are provided. The test strips can be used for analysis of samples by methods including electrical and optical measurements. The reagent test strips and methods are particularly suited for use in the detection of blood coagulation.

14 Claims, 5 Drawing Sheets

U.S. PATENT DOCUMENTS

| | | |
|---|---|---|
| 6,696,240 B1 | 2/2004 | Kloepfer et al. |
| 6,699,718 B1 | 3/2004 | Bruegger |
| 7,005,857 B2 | 2/2006 | Stiene et al. |
| 7,090,802 B1* | 8/2006 | Wang et al. .................... 422/58 |
| 7,090,984 B2* | 8/2006 | Hashimoto et al. ........... 435/7.1 |
| 7,125,711 B2* | 10/2006 | Pugia et al. .............. 435/288.5 |
| 7,303,923 B2* | 12/2007 | Hardman et al. ............ 436/518 |
| 7,381,571 B2* | 6/2008 | Woudenberg et al. ....... 436/518 |
| 7,445,941 B2* | 11/2008 | Buechler .................... 436/514 |
| 2004/0115795 A1 | 6/2004 | Rees |
| 2004/0248306 A1* | 12/2004 | Hernandez et al. ............ 436/39 |
| 2007/0158246 A1* | 7/2007 | Davies et al. ................. 210/85 |

FOREIGN PATENT DOCUMENTS

| | | | |
|---|---|---|---|
| EP | 1482296 A1 | | 12/2004 |
| WO | WO 93/09439 A1 | | 5/1993 |
| WO | WO 95/06868 A1 | | 3/1995 |
| WO | WO 99/46591 A2 | | 9/1999 |
| WO | WO 99/46591 A3 | | 11/1999 |
| WO | WO 00/06761 A1 | | 2/2000 |
| WO | WO 2005043156 | * | 5/2005 |
| WO | WO 2005114140 | * | 12/2005 |

* cited by examiner

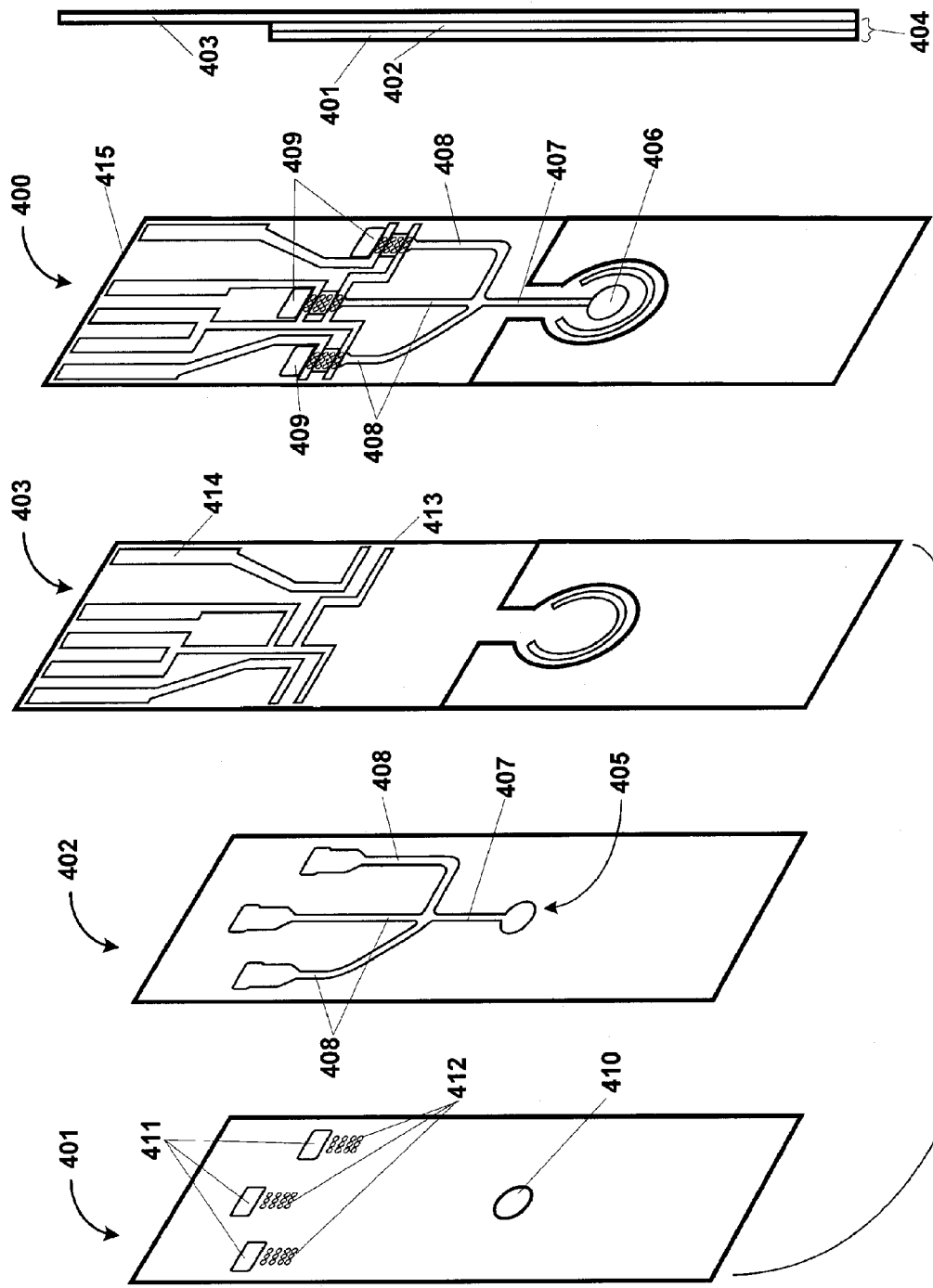

DEVICE AND METHOD FOR MEASURING PROPERTIES OF A SAMPLE

FIELD OF THE INVENTION

This invention relates to a test strip for determining the condition of a sample. The test strip comprises two or more capillary branch channels that convey the sample from a sample well to a measurement area. At least one of the branch channels delays the arrival of the sample to a control measurement area thereby ensuring that a test measurement area is filled first, and detecting when insufficient sample has been applied to the test strip to prevent or reduce the likelihood of a false result.

BACKGROUND OF THE INVENTION

Test strips are widely used for industrial and medical purposes. For example, industrial test systems use test strips for laboratory testing of water quality monitoring the levels of a variety of analytes including arsenic, cyanide and chlorine in effluents and surface waters. In medical settings, test strips are used, for example, to detect amino acids and proteins in urinalysis test, or to detect hormones in pregnancy tests. Most importantly, test strips are used for point of care testing that has been developed out of the need for clinicians to have rapid test results to improve the patient care process. In particular, test strips are used by millions of diabetics to monitor blood glucose levels, and by millions of patients who need to monitor the effects of oral anticoagulant therapy.

Because of the importance of obtaining accurate readings, in particular diagnostic readings related to medical conditions, it would be highly desirable to have a test strip that affords the user an increased reliability in obtaining a correct reading.

The present invention provides a test strip that automatically measures concurrently a sample test and at least one level of quality control on each test, and simultaneously determines whether sufficient sample was applied to the test strip and whether the control(s) are within preset limits. If they are not, the measuring device displays an error message.

SUMMARY OF THE INVENTION

In general, the invention provides a test strip designed to prevent or reduce the likelihood of false results when measuring a condition of a sample. The invention also provides a method for detecting the condition of a sample; and a system that includes the test strip and a measuring device.

In some embodiments, the invention provides a test strip for determining the condition of a sample wherein the test strip comprises at least two branch channels each fluidly connected to a different reaction chamber, and wherein at least one of said branch channels is a delaying branch channel and at least one of said branch channels is a non-delaying branch channel, wherein the delaying branch channel is adapted to delay arrival of a portion of the sample to its reaction chamber with respect to arrival of a second portion of the sample to the non-delaying branch channel reaction chamber. In some embodiments, the reaction chamber of the delaying channel detects an error in the test strip. In one embodiment, the condition of the sample is the quantity and/or presence or absence of an analyte. In another embodiment, the condition is the degree of the ability of a sample to coagulate or lyse.

In some embodiments, the delaying branch channels of the test strip of the invention are longer than the non-delaying branch channels. In other embodiments, the delaying branch channels are narrower than the non-delaying branch channels. In yet other embodiments, the delaying branch channels are longer and narrower than the non-delaying branch channels. Alternatively, the delaying branch channels are partially occluded by an obstacle. In some embodiments, the obstacle is less wettable than the branch channel. In one embodiment, the reaction chambers are configured for the detection of coagulation or lysis time of a fluid sample. In one embodiment, the test strip comprises a delaying branch channel that prolongs the time it takes a sample to fill the reaction chamber to which the delaying branch channel is coupled.

In one embodiment, the invention provides a test strip for determining the condition of a sample comprising at least two branch channels each fluidly connected to a different reaction chamber, wherein at least one of said branch channels is a delaying branch channel and at least one of said branch channels is a non-delaying branch channel, wherein the delaying branch channel is adapted to delay arrival of a portion of the sample to its reaction chamber with respect to arrival of a second portion of the sample to said non-delaying branch channel reaction chamber, and wherein at least one of said delaying branch channels is fluidly connected to a control reaction chamber, and wherein at least one of said non-delaying branch channels is fluidly connected to an assay reaction chamber. In another embodiment, the condition of the sample is determined as an electrical or optical property of said sample. In another embodiment, the assay and control chambers comprise reagent compositions for measuring prothrombin time (PT). In yet another embodiment, each of the reaction chambers of the test strip comprises an electrode pair for measuring a parameter of coagulation of said sample in said reaction chamber.

In some embodiments, the invention provides a test strip for determining the condition of a sample wherein the test strip comprises at least two branch channels each fluidly connected to a different reaction chamber, and wherein at least one of said branch channels is a delaying branch channel and at least one of said branch channels is a non-delaying branch channel, and wherein at least one reaction chamber of said non-delaying branch channels comprises a reagent that activates the coagulation of said fluid sample for determining one of prothrombin time (PT), activated clotting time (ACT), activated partial prothrombin time (APTT), or thrombin clotting time (TCT). In other embodiments, at least one of the reaction chambers of the test strip comprises tissue factor.

In some embodiments, the invention provides a system for measuring a parameter of coagulation or lysis of a sample, said system comprising:

(a) a test strip comprising at least two branch channels, wherein each of said branch channels is fluidly connected to a different reaction chamber, wherein at least one of said branch channels is a delaying branch channel fluidly connected to a delaying reaction chamber and at least one of said branch channels is a non-delaying branch channel, wherein the delaying branch channel is adapted to delay arrival of a portion of the sample to its reaction chamber with respect to arrival of a second portion of the sample to the non-delaying branch channel reaction chamber; and (b) a measuring device comprising an inlet port for receiving said test strip and measuring a parameter of coagulation or lysis in said non-delayed chamber.

In other embodiments, the system of the invention comprises a test strip comprising at least two branch channels, wherein each of said branch channels is fluidly connected to a different reaction chamber, wherein at least one of said branch channels is a delaying branch channel fluidly connected to a delaying reaction chamber and at least one of said branch channels is a non-delaying branch channel, wherein at least one of said delaying reaction chambers comprises reagents formulated to coagulate said sample within a predetermined normal range. In other embodiments, at least one of said delaying reaction chambers of the test strip of the system comprises reagents formulated to coagulate said sample within a predetermined therapeutic range. In some embodiments, the system of the invention comprises a device that is configured to signal an error message when said sample does not coagulate within said predetermined range.

In other embodiments, the system of the invention comprises a device that is configured to signal an error message when at least one of said delaying branch channels is not filled with said sample. In yet other embodiments, the device of the system is further configured to signal an error message when said sample does not coagulate within said predetermined range.

The invention also provides a method for determining the condition of a sample comprising:
(a) applying a sample to a sample well of a test strip
(b) conveying a first portion of said sample from said sample well to an assay chamber;
(c) conveying a second portion of said sample from said sample well to a control chamber, wherein said second portion is delayed in reaching said control chamber with respect to the arrival of said first portion in said assay chamber. In some embodiments, the step of delaying the sample detects an error in the test strip. In other embodiments, the method of the invention comprises detecting an electrical or an optical characteristic of said sample.

In one embodiment, the invention provides a method of fabricating a test strip for measuring the condition of a fluid sample comprising: providing a laminate having three layers; and microfabricating on one of the three layers a fluidic path that comprises a feeder channel coupled to at least two branch channels, wherein each branch channel is coupled to a different reaction chamber, and wherein one or more delaying branch channels are adapted to delay a fluid sample from reaching said reaction chamber. In some embodiments, the reaction chambers are adapted to coagulate or lyse a sample. In other embodiments, at least one of the delaying branch channels comprises a control formulation.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4A-C illustrates a process for fabricating a test strip.

DETAILED DESCRIPTION OF THE INVENTION

Figure 1A:
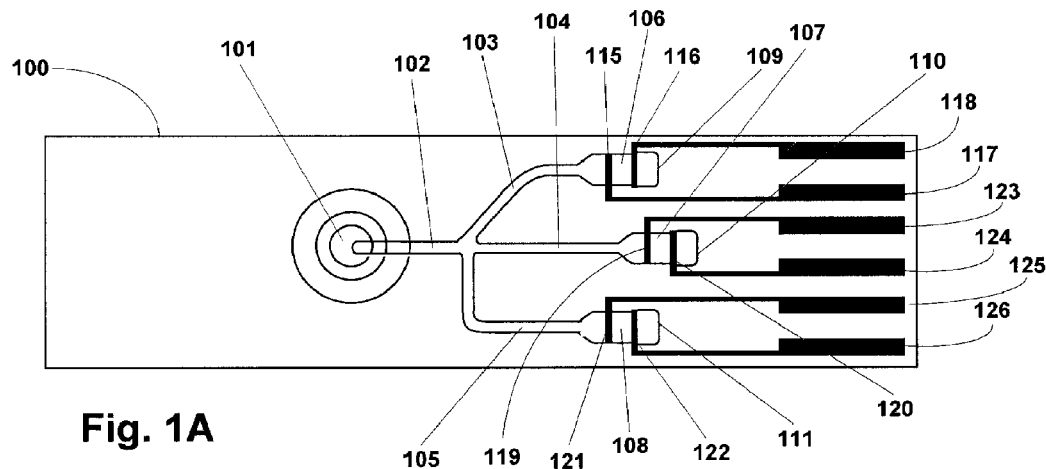
FIGS. 1A-B illustrate a top view of two configurations of a test strip.

The invention relates fluidic systems for analyzing a fluidic sample. The fluidic systems can include one or more test chambers and one or more detection modules. The test chamber and detection module can be configured to prevent or reduce false results in the analysis step. Such a result can occur, for example, due to insufficient fluid sample or improper operation of the system. A fluid system can have any size, shape, or dimension. In some cases, the fluidic system comprises two or more branched channels each of which comprises a reaction chamber for performing an analysis on a portion of the fluidic sample. In one embodiment, a fluidic system comprises a test strip, cartridge, cassette, card or slide comprising two or more reaction chambers for determining a parameter or condition of a patient. Such fluidic system, e.g., test strip, is optionally disposable.

The condition of a sample can be determined by any means known in the art. In some embodiments, a fluidic device herein determines a physical property of a sample (e.g., electrical property, magnetic property, photometric property, affinity, etc.).

Electrical properties that can be measured by the devices herein include, but are not limited to, electrochemical and electrical conductivity, and impedance. Impedance can be reflective of the change in viscosity or coagulation or lysis of a sample. Thus, coagulation or lysis of a sample can be measured as a function of a change in impedance, or it may also be measured as a function of a change in the electrolytic conductance of the sample. Electrolytic conductance is a measure of the ability of electrolytes in a solution to carry an electrical current by virtue of the mobility of the ions in the solution.

In some embodiments, electroactive chemical species can be added to the sample to enhance the electrolytic conductivity of a sample (e.g., uncoagulated blood), and increase the sensitivity and reliability of the measurement of electrolytic conductance. Changes in electrolytic conductance can also be used for measuring the condition of a sample such as the rate of lysis of a sample. Preferred electroactive species are water soluble and are capable of forming a redox couple. Electroactive species that can be used include but are not limited to ferricyanide, ferrocyanide, cadmium chloride, and methylviologen are most preferred electroactive species for use with the present invention.

In some cases, a device herein can be used to measure changes in the diffusion constant or kinetic profile of an electroactive species which is added to the blood sample as a function of time while the fluid undergoes clotting. Any electrochemical technique that allows the determination of the diffusion kinetics/constants of an electroactive substance is suitable for use with the present invention, including, for example polarography, cyclic voltammetry (CV), rotating disk voltammetry (RDV), chronoamperometry/chronocoulometry, chronopotentiometry and those techniques disclosed in U.S. Pat. No. 6,046,051 and E. Dayalan et al., "Micelle and Microemulsion Diffusion Coefficients", Electrochemistry in Colloids and Dispersion, VCH Publishers, Inc. New York 1992 and the references cited therein.

Photometric measurements that can be measured by the devices herein use any form of light including ultraviolet, visible and infrared. In some embodiments, the devices herein perform one or more photometric measurements using visible or ultraviolet light. In some embodiments, the devices herein measure light transmission, emission, absorption, and/or scattering. When an optical property is monitored, a change in light absorption, transmission, emission or scattering by the fluid is measured by the measuring device. The combination of assay reagents and analyte in the sample results in a change in optical properties that can be monitored by photometric measurements of light of different wavelengths including ultraviolet, visible and infrared. The results can be read visually or with an optical instrument. Typically, devices that are used to make photometric measurements provide a light source that is located adjacent to one surface of the devices herein and a detector is adjacent to the opposite surface (two parts of a reaction chamber). The detector measures light transmitted through a fluid sample. Alternatively, the light source and detector can be on the same side of the reaction chamber. Alternatively, light that is scattered from a fluid sample or light that passes through the sample and is reflected back through a second time (by a reflector on that opposite side) can be detected by a detector on the same side as the light source. The change in transmitted, emitted, scattered or absorbed light is a measure of the analyte or property of the sample of interest.

Other physical properties that can be measured by the devices herein to determine the condition of a sample include viscosity and magnetic properties.

Various conditions can be determined by the fluidic devices herein. In some embodiments, the condition of a sample to be determined is the ability of the sample to lyse or coagulate. In some embodiments, the condition of a sample to be determined is the quantity and/or presence or absence of an analyte in the sample.

A sample can be derived from a variety of sources, e.g. water sources, food sources, air or gas sources, an organism etc. In some cases a sample is a fluid sample and is derived from an organism such as an animal or a human. Examples of specimens derived from a human include mucous, sweat, tears, ear flow, sputum, lymph, bone marrow suspension, lymph, urine, saliva, serum, plasma, whole blood, semen, vaginal flow, cerebrospinal fluid, brain fluid, ascites, milk, secretions of the respiratory, intestinal or genitourinary tracts fluid and pericardial, peritoneal, pleural or other like washes.

In addition, samples that are not pathologic samples can also be tested using the fluidic devices herein. For example, buffered solutions, extracted solutions, and water can be tested, for example, for the quantity and/or presence of an analyte such as presence of a pathogen or for the presence of a particulate contaminant.

Thus, an analyte in the sample can be a clotting factor, antibody, growth factor, antigen, or cytokine. Other analytes of interest may be an enzyme, a DNA fragment, an intact gene, a RNA fragment, a small molecule, a metal, an environmental agent, a nucleic acid, a cytoplasmic component, pili or flagella component, protein, polysaccharide, drug, or any other material. Analytes that may be specific to an infectious agent such as a bacterial, viral or fungal agent may include polysaccharide, an enzyme, a nucleic acid, a membrane component, or an antibody produced by the host in response to the bacteria. In some embodiments, the quantity and/or presence or absence of the analyte may indicate an infectious disease, cancer or other metabolic disorder or condition. In other embodiments, the quantity and/or presence or absence of the analyte may be an indication of food poisoning or other toxic exposure. A quantity and/or presence or absence of an analyte in a sample may also be an indication of the presence of biological warfare (e.g. anthrax), water contamination or drug abuse or may be an indication of the effectiveness of therapeutic agents. In some cases, a sample is a blood sample or a plasma sample derived from an animal or a human and the analyte whose quantity is determined is a clotting factor. The determination of an amount of a clotting factor provides information on the condition of the sample—its ability to coagulate or lyse.

In some embodiments, a reagent used to detect an analyte is characterized by its ability to specifically bind the analyte or analytes of interest. In some embodiments, reagents used in the devices herein can comprise toxins, antibodies, antigens, hormone receptors, parasites, cells, haptens, metabolites, allergens, nucleic acids, nuclear materials, autoantibodies, blood proteins, cellular debris, enzymes, tissue proteins, enzyme substrates, coenzymes, neuron transmitters, viruses, viral particles, microorganisms, proteins, polysaccharides, chelators, drugs, etc.

Figure 1B:
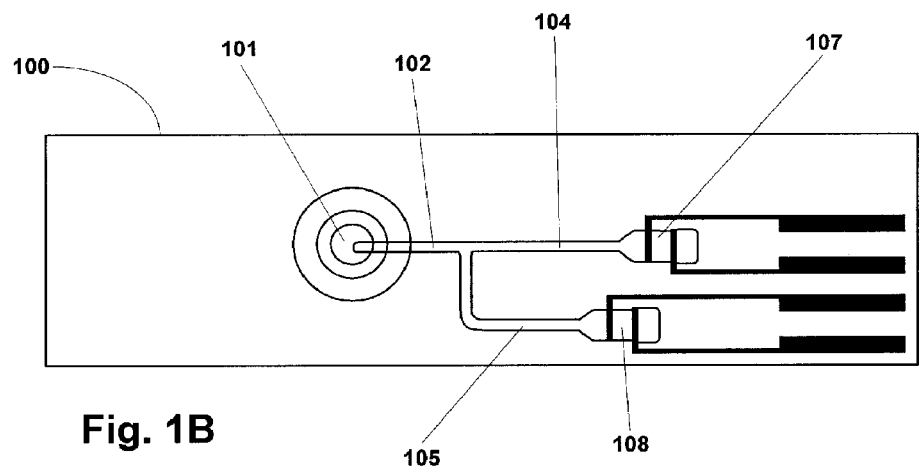
Figure 2:
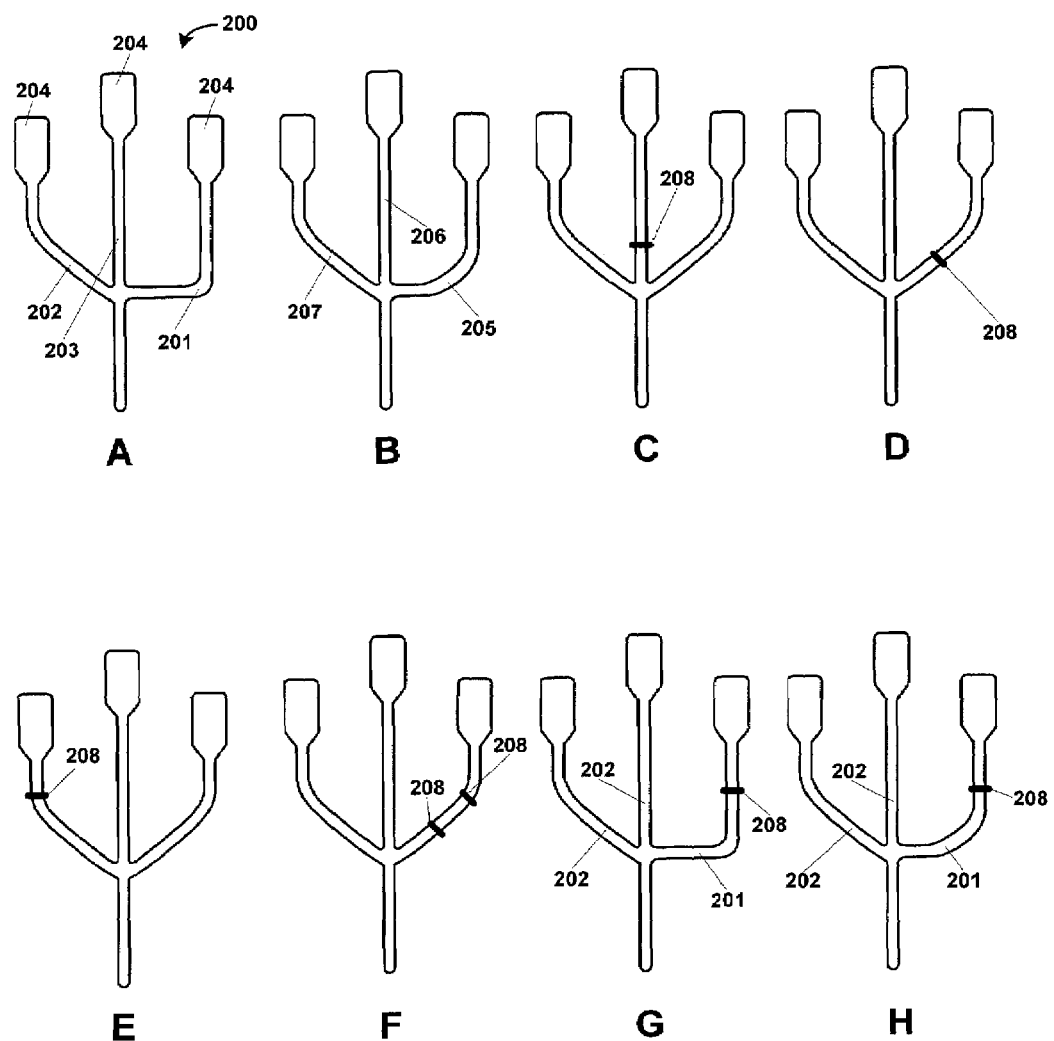
FIGS. 2A-H illustrate several embodiments of fluidic paths of a test strip.

Two embodiments of devices contemplated herein are shown in FIGS. 1A-B, which show a top view of a fluidic device. The fluidic devices herein can have various dimensions. In some cases, a fluidic device such as in FIGS. 1A-B, is a test strip or cartridge which can be used in combination with a detection device to analyze condition of a sample. The devices (e.g., test strips) herein can be used to measure a physical property of a sample applied to them. Such physical property can be, for example an electrical property such as impedance.

The embodiment shown in FIG. 1A is a fluidic device, e.g., a test strip, 100 that comprises a sample well 101 that is open to the atmosphere. To use the device herein, a sample is deposited into sample well 101. The sample deposited can be of any volume. In some cases, a sample volume is greater than 1, 10, 100 mL. In some cases, a sample volume is up to 1, 0.1, or 0.01 mL. The sample well 101 can be fluidly coupled to a microfluidic feeder channel 102 that is subdivided into two or more branch channels. Or in the alternative (not shown) a sample well can be immediately subdivided into two or more branch channels. In FIG. 1A, feeder channel 102 is subdivided into three branch channels 103, 104, and 105. Each branch channel ends in different reaction chambers 106, 107, and 108. The dimensions of each of the branch channels can vary depending on the sample volume being analyzed or other factors. In some embodiments, a branch channel of a device herein has a diameter greater than 0.01, 0.1 or 1 mm. In some embodiments a branch channel of a device herein has a diameter that is up to 0.01, 0.001, or 0.0001 mm.

During use, a sample (e.g., water sample, blood sample, etc.) is applied to the sample well 101, and is transported by the flow force or capillary action through the branch channels 103, 104, and 105 to the reaction chambers 106, 107, and 108. Sample flow is stopped within each of the reaction chamber(s) by air vents 109, 110, and 111 that act as stop junctions.

Each of the reaction chambers can optionally comprise one or more assay reagents. Such assay reagents can be used to determine the condition of a sample. In one example, an assay reagent is a reagent that induces coagulation or lysis. In another example, an assay reagent is a reagent that detects the quantity and/or presence or determines the absence of an analyte in a sample. The reaction chamber can also contain a detector for detecting such change in the sample. As shown in the embodiment of FIGS. 1A-B, the detector for detecting electrical properties of a sample or level of coagulation or lysis of a sample or the quantity and/or presence of an analyte can comprise a pair of electrodes. A pair of electrodes can include a driver electrode (117, 123 and 125) and a receiver electrode (118, 124 and 126, respectively). The driver electrodes 117, 123 and 125 deliver a current to the reaction chambers 106, 107, and 108. The receiver electrodes 118, 124, and 126 deliver an electrical signal reflective of the electrical properties of the sample present in the reaction chambers to a measuring device that translates the electrical signal into a digital output. The current that is provided by the driver electrodes 117, 123 and 125 enters the reaction chambers via a proximal end 115, 119, and 121 of the driver electrodes. The proximal end 116, 120, 122 of the receiver electrodes 118, 124, and 126 are positioned within the reaction chamber distal to the proximal ends of driver electrodes 115, 119 and 121.

The current that is detected and signaled by the receiver electrode(s) 118, 124 and 126 is indicative of the electrical properties of the sample in the reaction chamber(s) 106, 107 and 108. In some cases, the electrical properties of the sample reflect a condition that reflects the degree or ability of a sample to lyse or coagulate. The ability of a sample to lyse or coagulate can be determined as a measurement of a parameter of coagulation or lysis. For example, a parameter of coagulation or lysis can be the rate of coagulation or lysis. In some cases, the electrical properties of the sample are used to detect the quantity and/or presence or absence of an analyte in the sample. Repeated measurements can be signaled over a period of time to provide a measurement indicative of the condition that is being tested.

When analyzing optical properties of a sample, the driving electrode(s) and receiving electrode(s) can be substituted by light emitter(s) and emitter detector(s) respectively. Other modules used to detect properties of a sample can also be used (e.g., magnets and magnetic detectors).

In one embodiment, at least one of the reaction chambers 107 is an assay reaction chamber that comprises one or more reagents that modulates or triggers a reaction with the sample (e.g., activate the clotting of a sample), and at least one of the reaction chambers 108 is a control reaction chamber. A control chamber can comprise one or more reagents that modulates or triggers a reaction within a predetermined range of time or with predetermined characteristics (e.g., amount of reactivity). In some cases, a control chamber induces the clotting of a sample to occur within a predetermined range of time.

Typically, a control reaction chamber 108 is coupled to the microfluidic feeder channel 102 through a branch channel 105 that delays the arrival of a portion of the sample into the control reaction chamber with respect to the arrival of a second portion of the sample in the assay reaction chamber 107. The delayed arrival ensures that the assay reaction chamber 107 is filled before the control reaction chamber 108. As discussed above, the control reagents (and detectors) will vary depending on the type of test that is being performed on the sample. For example, control reagents for a test for the quantity and/or presence or absence of a pathogen could lack the antibody that would be used to bind the pathogen, while the test reagents could include such antibody(ies).

In one embodiment, a device herein can comprise branch channels that differ in length. In one embodiment, one or more branch channels are delaying branch channels that prolong the arrival of the fluid sample to its corresponding reaction chamber, and one or more branch channels are non-delaying branch channels that do not delay the sample from arriving to the reaction chamber. Examples of fluidic devices that comprise delaying and non-delaying branch channels are shown in FIGS. 1-5.

In the embodiment shown in FIG. 1A, the fluidic device (e.g., test strip) has at least one branch channel 105 that delays the arrival of the fluid sample (e.g., blood) to its corresponding reaction chamber 108. In this embodiment, the delaying branch channel corresponds to a first control channel 105, while the assay channel 104 and a second control channel 103 are non-delaying channels. This configuration ensures that the sample fills the assay chamber coupled to the non-delaying channel before it fills the control chamber that is coupled to a delaying channel to ensure that a true assay result is obtained. Thus, a control result invalidated due to insufficient sample size in the control chambers raises a question about the sufficiency of the sample size in the assay reaction chamber and therefore calls into a question an otherwise plausible assay result. For example, when insufficient sample (one that does not fill completely fill the reaction chambers of the delaying and non-delaying channels) is applied to the device herein, a portion of the sample fills the assay chamber while the remaining amount may not fill or may only partially fill the first control reaction chamber 108 that is positioned at the end of the delayed (e.g., longer) control branch channel 105. A control chamber that does not receive any sample or that is only partially filled with a sample will provide a readout value of the sample characteristic that is being measured that would be outside of a pre-established normal or control range and potentially very different form the assay chamber reading. The absence of sample from the control chamber or an insufficient amount of sample in the control chamber generates an error message or a message alerting the user that the sample volume was insufficient and that the reading from the assay chamber may be unreliable.

In some instances, the amount of sample is so insufficient that the assay chamber will also not be filled, an error message will be generated. At this time, a user may wish to retest or simply record the valid assay result. On the other hand, if both chambers receive sufficient sample to derive readings within the pre-set range, and if the readings are largely in agreement with each other, then the user can be confident that the assay result is based on a sufficient sample size. When the fluidic device herein is used to test a small sample (e.g., blood sample), an insufficient sample may be one that is up to 5, 4, 3, 2, or 1 μL.

In another embodiment, the delaying channel 105 and the respective reaction chamber 108 serve as a control channel and control reaction chamber respectively, while non-delayed branch channels 103 and 104 and their respective reaction chambers 106 and 107 serve as a first and a second assay channel and assay reaction chambers respectively.

In the embodiment shown in FIG. 1B, a fluidic device herein such as a test strip comprises one delaying control channel 105, (a subset of all branch channels) and one non-delaying assay branch channel 104. Branch channel 105 delays the arrival of the sample to control reaction chamber 108 to ensure the preferential fill of assay reaction chamber 107 by assay branch channel 104. In some embodiments, delaying branch channel 105 delays the sample by not more than 5 seconds. In other embodiments, the delay is of no more than 3, or 2, or 1, or 0.5 seconds.

Delaying the arrival of the sample in one or more reaction chambers (e.g. control reaction chambers) can be achieved by any means known in the art. For example, the delaying branch channels (e.g. at least 1, 2, or 3 of all branch channels) may be longer or have a smaller diameter than the non-delaying branch channels, or the delaying channels may be longer and have a smaller diameter than the non-delaying branch channels.

FIGS. 2A-H illustrate various examples for delaying flow through one or more delaying channels. FIG. 2A shows a fluidic path 200 of a fluidic device similar to the one described in FIG. 1A. It comprises one branch channel 201 that delays the arrival of the sample to a control reaction chamber 204 by being longer than the remaining two non-delaying branch channels 202 and 203. The reaction chambers coupled to the non-delaying branch channels can be both assay chambers or one can be an assay reaction chamber and the other can be a second control reaction chamber. The delaying branch channel 201 of the embodiment of FIG. 2A is about 24% longer than the nominal length of the remaining branch channels 202 and 203.

Alternatively, as shown in FIG. 2B, the delaying channel 205 can be configured to be 13% longer than the nominal length of the remaining branch channels 206, 207. In some embodiments, the nominal length is 0.8". Thus, in some embodiments, the delaying branch channel can be at least 5%, 10%, 15%, 20% or 25% longer than the non-delaying branch channel(s).

FIGS. 2C, 2D, 2E and 2F show embodiments of a fluidic path wherein the delay in a delaying branch channel is provided by one or more obstacles 208 in the branch channel. In the embodiments of FIGS. 2C-2E, the delaying and non-delaying branch channels are of equal length and diameter. Obstacles 208 narrow the delaying branch chambers in which they are situated by narrowing the channel without occluding it. Obstacles can be made of any inert substance that would not affect the condition of the sample and they can be made using the same material that can be used for fabricating the electrodes, e.g. silver, carbon, gold or platinum. In some embodiments, the obstacles are less wettable than the channel walls, thereby further delaying the arrival of the sample to the reaction chamber. Materials such as Ag/AgCl can be used to make the obstacles less wettable. The obstacles can be deposited in the same manner and at the same time during which the electrodes are formed.

In other embodiments as shown in FIGS. 2G and 2H, fluidic paths may comprise delaying branch channels 201 that include one or more obstacles 208 and are longer or have a wider diameter or both than the non-delaying channels 202. In any of the embodiments herein, preferential filling of the assay chamber may also be ensured by providing an assay branch channel that has a smaller diameter than that of the delaying branch channels. For example, the delaying branch channel can have a diameter that is about 30% smaller than that of the non-delaying branch channel that leads a sample to an assay reaction chamber. In other embodiments, the delaying branch channel has a diameter that is narrower by up to 10%, 20%, 30%, or 40% than that of a non-delaying branch channel. In one embodiment the diameter of the non-delaying branch channel is 0.060", and the diameter of the delaying branch channel is 0.040". Alternatively, the strip may comprise a non-delaying assay branch channel that is wider and shorter than the delaying control branch channels. For example, the delaying control branch channel can be narrower than the non-delaying channel by up to 10%, 20%, 30%, or 40%. The delaying control branch channel can also be longer than the non-delaying channel by up to 10%, 15%, 20% or 25%. In one embodiment, the delaying branch channel can delay the filling of the control chamber by up to 1, 2, 3, 4, or 5 seconds or 1, 2, 3, 4, or 5 minutes. In other embodiments, the delaying branch channel can delay the filling of the control chamber by at least 1, 2, 3, 4, or 5 seconds or 1, 2, 3, 4, or 5 minutes.

Alternatively, the delaying branch channels may differ from the non-delaying branch channels in diameter, or they may differ in length and diameter, and the diameter may be constant or it may vary along the length of the channel. Preferably, at least one of the branch channels is longer than the rest. The rate at which a liquid penetrates a horizontal capillary under its own capillary pressure is directly proportional to the capillary radius and inversely proportional to the capillary length already filled by the liquid. As used herein, microfluidic channel generally refers to microcapillary feeder or branch channels of any suitable cross-section, and having a lateral dimension that is less than 1000 µm. The microfluidic channels of the devices herein may measure preferably less than 100 µm, or less than 50 µm. The length of the branch channels may be any length that is suitable for use within the dimensions of the test strip. However, it is likely that the length of the branch channels will be between 0.7 inch and 1.0 inch and such channel can have a volume of between 0.5 and 50 µl. Generally speaking, the difference in total volume of the delaying channel from the non-delaying channels will be between 5-25%. This increase in the volume of sample required to carry out an assay is correspondingly small, and it is easy and beneficial to provide an additional sample to rectify an unacceptable reading.

Any of the devices herein can be designed to be inserted into a measuring device suitable for measuring condition of the patient (e.g., the electrical or optical property of the sample) and providing an input to the user. When the fluidic device comprises electrodes to detect an electrical property in the sample, the fluidic device can be inserted into a measuring device such that the distal end of the electrode pair on the test strip engages with and makes electrical contact with corresponding electrical contact points of the measuring device. Electrical parameters measured by the electrodes are then transmitted to the measuring device which is able to interpret the signal in order to give a result. The electrodes may be of any suitable inert conductor and may be selected from amongst others, silver, carbon, gold or platinum. Preferably, the electrodes are made of silver, and may be produced by the printing of an ink onto the microfluidic channels or by other means of deposition such as vacuum or sputtering. The electrodes may be of any suitable shape or size and may be positioned within the reaction chamber(s) as pairs of driver and receiver electrodes, as shown in FIG. 1. When the fluidic device comprises light emitters and light detectors, a measuring device can detect the light traveling through the sample and provide information based on such parameters to the user. Similarly, a measuring device can detect magnetic or affinity properties of the sample.

Figure 3C:
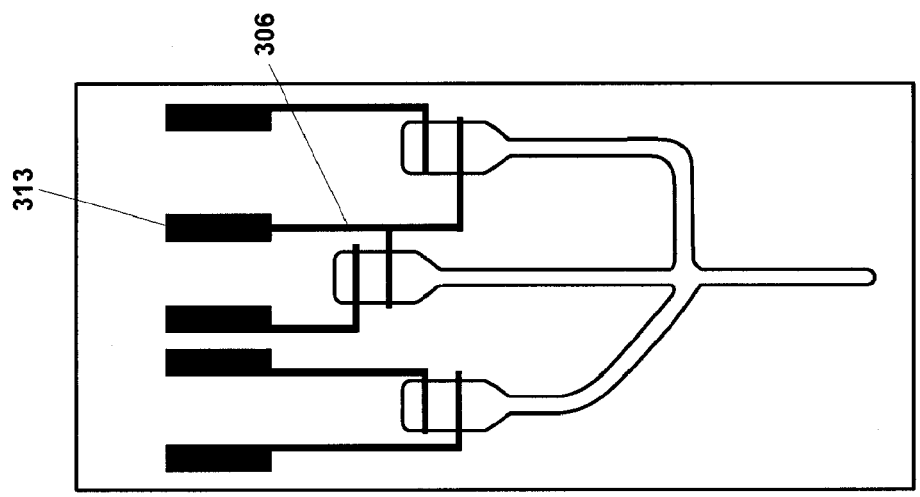
FIGS. 3A-C illustrate several embodiments of electrodes of a test strip.
Figure 3B:
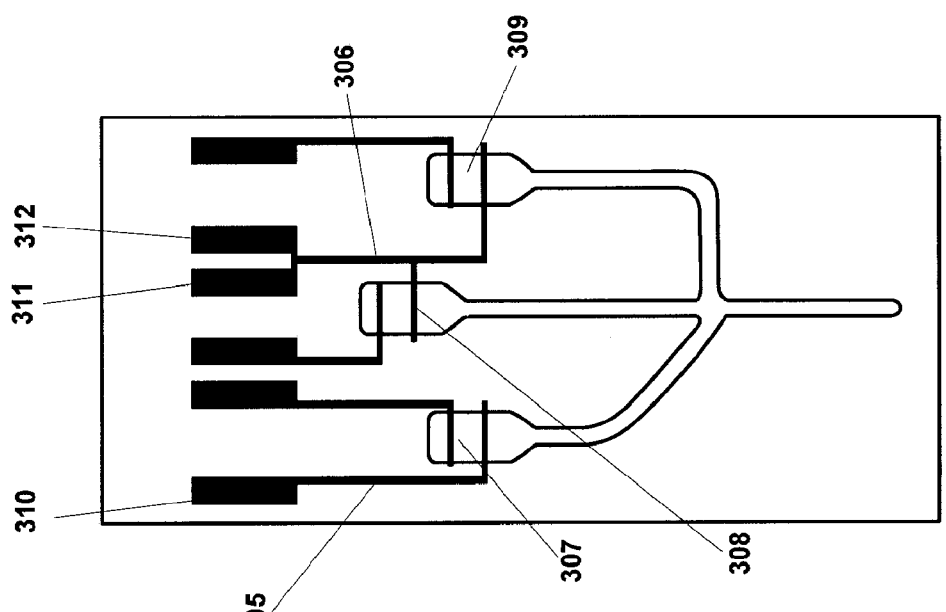
Figure 3A:
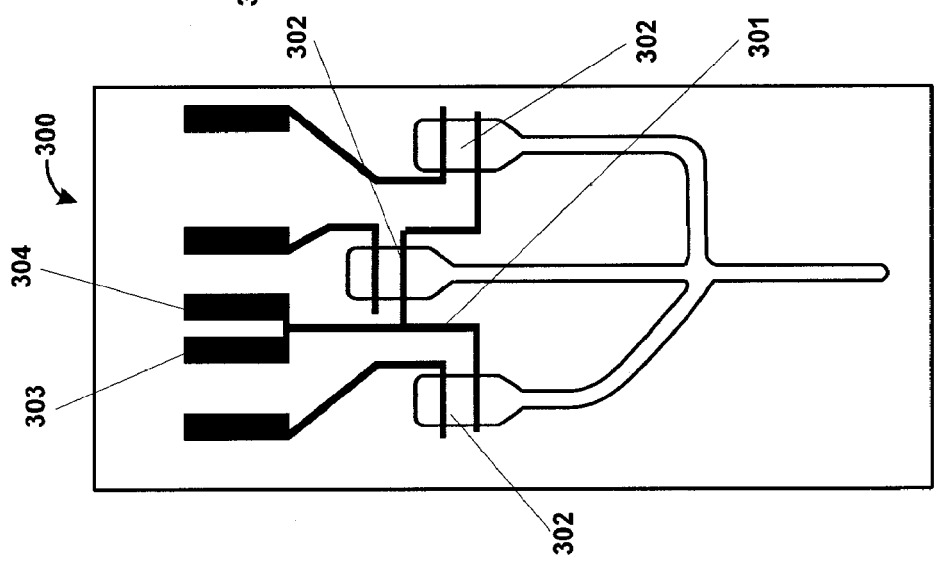

FIGS. 3A-3C illustrate alternative embodiments for electrode set ups. In some embodiments, an electrode (e.g., driving electrode) can extend across two or more chambers. In FIG. 3A, a single driver electrode 301 extends across all three reaction chambers 302, to provide a current that enters the test strip 300 via a first 303 and a second 304 distal end of receiver electrodes. In FIG. 3B, a test strip 300 has a first driver electrode 305 and a second driver electrode 306 driver electrode, wherein the first driver electrode 305 extends into a first reaction chamber 307, and the second driver electrode 306 extends across a second and third reaction chamber 308 and 309 respectively. The driver electrode supplies current to the first reaction chamber 307 via one distal end 310, while the second driver electrode 306 supplies current to the second 308 and third 309 reaction chambers via a second 311 and third 312 distal ends. Alternatively, as shown in FIG. 3C, the second driver electrode 306 can supply current to the second 308 and third 309 chambers via a single distal end 313. Therefore, it is understood that any embodiment of the test strip can comprise one or more driver electrodes that supply a current to individual reaction chambers via one or more distal ends, each providing an individual proximal end to each reaction chamber.

The fluidic devices described herein can be fabricated by any means known in the art.

In some embodiments, when the fluidic devices are designed to analyze smaller samples, such devices can be fabricated as laminates using microfabrication methods that include, e.g., embossing and plasma etching, or by methods that use injection molding. The most suitable method for fabricating the device is chosen according to its intended use. For example, a device used to measure magnetic properties of a sample can include magnetic particles within its reaction chambers. Alternatively, a device used to measure an electrical property of a sample can include electrodes within its reaction chamber.

One method for fabricating a test strip for measuring electrical properties of a sample such as a blood sample is shown in FIG. 4. In this example, he test strip can be produced as a laminate that preferably comprises three layers 401, 402 and 403, as shown in the embodiment depicted in FIG. 4A. Layer 401 is the top layer; layer 402 is the middle layer, and layer 403 is the bottom electrode layer. The assembled strip 400 (FIG. 4B) is obtained by first assembling the top layer 401 and middle layer 402 to form a top-middle layer 404 (illustrated in FIG. 4C), and then combining the top-middle layer 404 with the electrode layer 403.

As illustrated in FIG. 4A, the fluidic path 405, which transports the sample from the sample well 406 through the microfluidic feeder 407 and branch channels 408 to the reaction chambers 409 of the assembled strip, can be formed by microfabricating a cutout on a two-sided adhesive middle layer 402. The top layer 401 which is made of nonporous material is perforated to provide a circular opening 410 that aligns with the portion of the microfluidic path 405 that forms the sample well 406 in the assembled test strip 400. Additional cutouts of the top layer 401 can be made to provide the air vents 411, which act as stop junctions during use of the strip. The top layer houses the reagents or compositions that enable the coagulation or lysis of a sample during use of the test strip. The reagents are deposited in the reagent areas 412 that are below the cut of the air vent, and on the side of the top layer that is adjacent to the middle layer. The adhesive is removed from the a first side of the middle layer 402 that is adjacent to the top layer 401, and the top 401 and middle layer 402 are assembled to form the top-middle layer 404 (FIG. 4C). The electrodes are formed on the electrode layer 403 by depositing a suitable inert conductor using a pump or any other means of deposition, such as vacuum or sputtering. Electrodes may also be produced by the printing of an ink using methods known in the art, such as screen printing. Suitable conductor materials that can be used to form the electrodes include but are not limited to silver, carbon, gold or platinum. The electrodes have a proximal end 413 and a distal end 414, which respectively span the region of the electrode layer 403 that is complementary to that defining the reaction chamber 409 and the signaling edge 415 of the assembled test strip 400. The adhesive is removed from the second side of the middle layer 402 of the top-middle layer assembly 404, and is adhered to the electrode layer 403 to form the assembled strip.

In some embodiments, the devices herein are used to measure the ability of a sample to coagulate or lyse. In such embodiments, a portion of the sample (e.g. plasma or whole blood) reaches the reaction chamber that includes one or more reagent compositions that activate the intrinsic and/or extrinsic coagulation cascade, and the time until clot formation is measured.

Examples of coagulation or lysis assays that can be performed independently or in combination in a reaction chamber include, but are not limited: the prothrombin time (PT), the activated clotting time (ACT), the activated partial prothrombin time (APTT), the thrombin clotting time (TCT) or the auto hemolysis test (AHT). Specific examples of tests that can be used in the reaction chambers are disclosed in more detail below.

The PT test was first described by Quick in 1935. The PT test measures the tissue factor-induced coagulation time of blood or plasma. It is used as a screening test to evaluate the integrity of the extrinsic coagulation pathway and is sensitive to coagulation factors II, V, VII, and X. A prolonged clotting time suggests the presence of an inhibitor to, or a deficiency in, one or more of the coagulation factors of the extrinsic pathway. The PT time can also be prolonged for patients on anticoagulant therapy, for example, coumarin drug therapy, or for those with vitamin K deficiency or liver dysfunction. Thus the PT test can provide an assessment of the extrinsic coagulation pathway. PT test results can be converted to International Normalized Ratio (INR) values according to the following formula:

$INR=(PT\ ratio)^{ISI}$, and PT ratio=Patient's PT/Mean Normal PT, where ISI is the International sensitivity index.

A device used to test PT may include, within one or more of its reaction chambers reagents that use appropriate for measuring PT, such prothrombin (e.g., recombinant or purified).

The ACT test is used primarily to monitor a patient's coagulation status in connection with clinical procedures that involve the administration of high doses of heparin (e.g., coronary bypass surgery and percutaneous transluminal coronary angioplasty). Prolongation of ACT is directly proportional to the concentration of heparin in the blood. A device used to test ACT may include within one or more of its reaction chambers reagents that use appropriate for measuring ACT, such as kaolin or celite.

The APTT test is used to evaluate the intrinsic coagulation pathway, which includes factors I, II, V, VIII, IX, X, XI, and XII. APTT test is used to assess the overall competence of a patient's coagulation system, as a preoperative screening test for bleeding tendencies, and as a routine test for monitoring heparin therapy. Thus, a device of the invention used to test APTT may include, within one or more of its reaction chambers, reagents that are appropriate for measuring APTT, such as partial thromboplastin (cephalin or soya phosphatide) and calcium chloride.

The TCT test measures the rate of a patient's clot formation compared to that of a normal plasma control. The TCT test can be used as an aid in the diagnosis of disseminated intravascular coagulation (DIC) and liver disease. Thus, a device of the invention may include, within one or more of its reaction chambers, reagents that are appropriate for measuring TCT, such as thrombin.

In any of the embodiments herein, different coagulation or lysis promoting reagents may be provided within different reaction chambers to allow for the simultaneous measurement of two or more different coagulation times. For example, in some embodiments PT and APTT assays might be carried out simultaneously each in a different reaction chamber. In some cases the PT or the APTT test is in a delayed reaction chamber and the other is in a non-delayed reaction chamber. Typically, the reagent compositions for the specified test are applied to the test strip during the manufacturing process of the test strip and using various types of microdispensing techniques which include, but is not limited to, ink jet, striper and sprayer deposition methods, or dip coating, and air dried in situ during the manufacturing process.

In some cases, a sample may be assayed for the thrombolytic effect of a drug, and lysis of a blood sample is monitored. The effect of plasminogen activators can be monitored by assaying the rate of coagulation of a sample from a patient receiving a thrombolytic drug, such as urokinase or tPA. The clotting or lysis time of the patient sample may then be compared to the clotting or lysis time of pooled normal plasma or whole blood to provide a standard measurement of the patient's hemostatic status.

In some cases, a sample is collected from a patient before the patient is administered a drug (e.g. urokinase or tPA) and after drug administration. A difference in coagulation level, lysis, presence or absence or amount of an analyte in a sample can be determined using the devices herein. This can be used to determine effectiveness of drug treatment.

Figure 5:
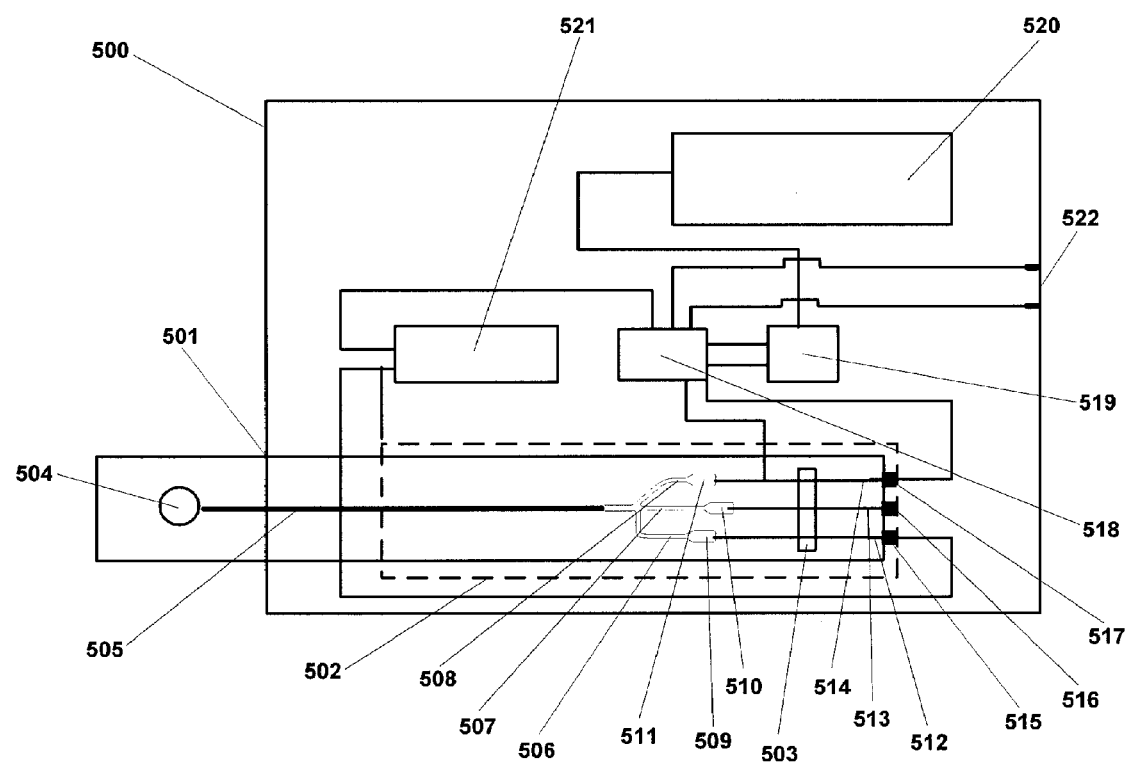
FIG. 5 illustrates a test strip in combination with a measuring device.

Use of a device herein that measures an electrical property of a sample can be understood with reference to an illustration of the elements of the measuring device shown in FIG. 5. The measuring device includes a housing 500 having an inlet port 501 for receiving a fluidic device. The fluidic device is inserted into the measuring device which provides information to the user about the physical properties of the sample. In some embodiments, the inserted fluidic device is positioned in proximity of a temperature control module (e.g., heater) 502 which keeps the sample at a predetermined temperature (e.g. room temperature or cooler). Temperature of a sample can optionally be maintained constant by signaling from a temperature sensor 503 to the temperature control module. The sensor is mounted in proximity to the detection area of the device, or it may be mounted anywhere on the device, and it provides temperature information for calibrating the device and ensuring that the assays are conducted at a predetermined constant temperature to eliminate interassay temperature variations.

When a sample is applied to the sample well 504 of the test strip, it can be transported through the microfluidic feeder channel 505 and branch channels 506, 507 and 508 by capillary action or fluid flow forces to the reaction chambers 509, 510, and 511. The volume that is applied to the device can vary depending on the sample. When the sample is a blood sample, a total volume of up to 50, 40, 30, 20, 15, 10, or 5 µl may be applied to the device. When the sample reaches the reaction chamber, it reacts with the reagent(s). The reaction is than measured by the measuring device. When the reaction chamber has a pair of electrodes, the reaction sample bridges the electrodes, thereby changing the resistance or capacitance across the electrodes and signaling the change to the measuring device. For example, the change in resistance is signaled through the distal end of the receiver electrodes 512, 513, and 514 that are in contact with corresponding contact pads 515, 516, and 517 of the measuring device to an analog to digital converter 518, which integrates the signal from the electrodes and conveys it to a processor and memory component 519, and a display 520. The device is driven by a source 521 that can be any power source such as a battery or a solar powered cell.

The processor 519 may have the capacity to either store a set of pre-programmed calibration information or have the capability to be programmed during device manufacturing. Appropriate calibration information may be stored in the device during manufacturing by laser burning the apposite circuit pathways. Alternatively, the appropriate calibration information may be downloaded onto the processor of the manufactured measuring device via the external ports 522 of the device. External calibration can be accomplished with external electrical contacts or may be done with a non-contact method using radio waves, magnetic fields, pulse light, laser or the like. The non-contact method of calibration may be more practical and efficient from a manufacturing viewpoint.

The processor will also control the entire operation of the instrument including, but not limited to, turning the instrument on in response to insertion of a test card, providing electrical power or time signals; timing with an on-board clock, recording, and processing the instrument zero function; controlling any time delays or timed steps during reading; determining when the assay has stabilized; receiving and processing information from the temperature sensor; and receiving input from measuring the electrical properties of the sample and converting it to output, based on calibration information, to the display 520. The processor will also determine if a reaction has occurred within a specified time to a specified endpoint range or within a specified reaction rate range to control for inactive reagents. Any other electronic control checks may also be included. The processor will also have stored calibration information. For example, calibration information can be stored such that a value of INR may be given as a result of a coagulation test. The processor contains a program which includes, but is not limited to, interpreting the current signals from the electrodes, relating the signal strength ratio to the reference strength, providing assay results, identifying potential errors, and performing other quality control checks. Examples of the information stored in the microprocessor includes, but is not limited to, algorithms or calibration curves for the analytes selected for analysis and other assay calibration information; reaction stabilization, endpoint, or rate information; and manufacturing lot information on each of the chemical reagents, detectors, LEDs, assay strips, and other components used in the device. Assay information can be relayed to the display from the processor, which, in addition to showing the assay results, may display messages related to the processing functions, and messages relating to the assay results including error messages.

The devices of the invention may also be used in combination with devices that measure changes in coagulation or lysis as a function of distance traveled by a sample along a substrate path or as a function of time required to travel along a substrate path. In addition, the devices of the invention may also be used in combination with devices that measure a change or the rate of change in impedance of a sample such as the coagulation or lysis of a sample by methods that use other than electrical signals, for example the test strip may be used with devices that measure changes in coagulation or lysis times using optical or colorimetric methods.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A test strip for determining the degree of the ability of a sample to coagulate comprising at least two branch channels each fluidly connected to a different reaction chamber, wherein at least one of said branch channels is a delaying branch channel and at least one of said branch channels is a non-delaying branch channel, wherein the delaying branch channel is adapted to delay arrival of a portion of the sample to its reaction chamber with respect to arrival of a second portion of the sample to said non-delaying branch channel reaction chamber, and further wherein at least one of said delaying branch channels is fluidly connected to a control reaction chamber, wherein at least one of said non-delaying branch channels is fluidly connected to an assay reaction chamber, and wherein the control reaction chamber comprises an electrode pair for measuring an electrical property of the sample.

2. The test strip of claim 1, wherein the reaction chamber of the delaying channel detects an error in the test strip.

3. The test strip of claim 1, wherein said delaying branch channel is longer than said non-delaying branch channel.

4. The test strip of claim 1, wherein said delaying branch channel is narrower than said non-delaying branch channel.

5. The test strip of claim 1, wherein said delaying branch channel is longer and narrower than said non-delaying branch channel.

6. The test strip of claim 1, wherein said delaying branch channel is partially occluded by an obstacle.

7. The test strip of claim 6, wherein said obstacle is less wettable than said branch channel.

8. The test strip of claim 1, wherein said reaction chambers are configured for the detection of coagulation or lysis time of a fluid sample.

9. The test strip of claim 1, wherein said delaying branch channel prolongs the time it takes a sample to fill a reaction chamber coupled to said delaying branch channel.

10. The test strip of claim 1, wherein at least one reaction chamber of said non-delaying branch channel comprises a reagent that activates the coagulation of said fluid sample for determining one of prothrombin time (PT), activated clotting time (ACT), activated partial prothrombin time (APTT), or thrombin clotting time (TCT).

11. The test strip of claim 1, wherein at least one reaction chamber comprises tissue factor.

12. The test strip of claim 1, wherein said assay and control reaction chambers comprise reagent compositions for measuring prothrombin time (PT).

13. The test strip of claim 1, wherein the condition is determined as an electrical property of said sample.

14. The test strip of claim 1 wherein each of said reaction chambers comprises an electrode pair measuring a parameter of coagulation of sample in said reaction chamber.

* * * * *